(12) United States Patent
Iizuka

(10) Patent No.: US 10,586,620 B2
(45) Date of Patent: Mar. 10, 2020

(54) DEVICE FOR CALCULATING AMOUNT OF RETAINED PHYSICAL ACTIVITY, METHOD FOR CALCULATING AMOUNT OF RETAINED PHYSICAL ACTIVITY AND SYSTEM FOR CALCULATING AMOUNT OF RETAINED PHYSICAL ACTIVITY

(75) Inventor: Hisashi Iizuka, Susono (JP)

(73) Assignee: TOYOTA JIDOSHA KABUSHIKI KAISHA, Toyota-shi, Aichi-ken (JP)

( * ) Notice: Subject to any disclaimer, the term of this patent is extended or adjusted under 35 U.S.C. 154(b) by 726 days.

(21) Appl. No.: 14/397,237

(22) PCT Filed: Apr. 27, 2012

(86) PCT No.: PCT/JP2012/061428
§ 371 (c)(1),
(2), (4) Date: Oct. 27, 2014

(87) PCT Pub. No.: WO2013/161072
PCT Pub. Date: Oct. 31, 2013

(65) Prior Publication Data
US 2015/0127265 A1    May 7, 2015

(51) Int. Cl.
| | | |
|---|---|---|
| *G01N 33/48* | (2006.01) | |
| *G16H 40/63* | (2018.01) | |
| *G16H 50/30* | (2018.01) | |
| *A61B 5/22* | (2006.01) | |
| *A61B 5/0476* | (2006.01) | |
| *A61B 5/11* | (2006.01) | |
| *G06F 19/00* | (2018.01) | |
| *A61B 5/00* | (2006.01) | |
| *A61B 5/024* | (2006.01) | |
| *A61B 5/16* | (2006.01) | |
| *A61B 5/08* | (2006.01) | |
| *A61B 5/18* | (2006.01) | |
| *A61B 5/0245* | (2006.01) | |
| *G06K 9/00* | (2006.01) | |

(52) U.S. Cl.
CPC ........... *G16H 40/63* (2018.01); *A61B 5/0022* (2013.01); *A61B 5/02405* (2013.01); *A61B 5/02438* (2013.01); *A61B 5/0476* (2013.01); *A61B 5/1118* (2013.01); *A61B 5/1123* (2013.01); *A61B 5/168* (2013.01); *A61B 5/22* (2013.01); *A61B 5/4812* (2013.01); *A61B 5/4866* (2013.01); *A61B 5/6898* (2013.01); *A61B 5/746* (2013.01); *G06F 19/3481* (2013.01); *G16H 50/30* (2018.01); *A61B 5/0002* (2013.01); *A61B 5/0048* (2013.01); *A61B 5/024* (2013.01); *A61B 5/0245* (2013.01); *A61B 5/0816* (2013.01); *A61B 5/162* (2013.01); *A61B 5/18* (2013.01); *A61B 5/4806* (2013.01); *A61B 5/6893* (2013.01); *A61B 5/7271* (2013.01); *A61B 5/7275* (2013.01); *A61B 2562/0219* (2013.01); *G06K 9/0053* (2013.01); *G06K 9/00845* (2013.01)

(58) Field of Classification Search
None
See application file for complete search history.

(56) References Cited

U.S. PATENT DOCUMENTS

| | | | |
|---|---|---|---|
| 4,502,122 A | 2/1985 | Yanagishima et al. | |
| 5,447,166 A * | 9/1995 | Gevins | A61B 5/0484 128/925 |
| 6,547,728 B1 * | 4/2003 | Cornuejols | G04B 25/04 600/300 |
| 2004/0049132 A1 | 3/2004 | Barron et al. | |
| 2005/0080344 A1 | 4/2005 | Nishii et al. | |
| 2007/0276270 A1 * | 11/2007 | Tran | A61B 5/0022 600/508 |
| 2008/0195166 A1 | 8/2008 | Sun et al. | |
| 2011/0028799 A1 * | 2/2011 | Hyde | G06F 19/3481 600/300 |
| 2011/0213269 A1 | 9/2011 | Harada et al. | |

FOREIGN PATENT DOCUMENTS

| | | |
|---|---|---|
| DE | 102 18 676 A1 | 11/2003 |
| JP | 2007-222276 A | 9/2007 |
| JP | 2010-063641 A | 3/2010 |
| JP | 2011-067241 A | 4/2011 |

* cited by examiner

*Primary Examiner* — Anna Skibinsky
(74) *Attorney, Agent, or Firm* — Sughrue Mion, PLLC

(57) ABSTRACT

A physical activity consumption amount calculation unit calculates the consumption amount of physical activity, which is the amount of physical activity consumed by a subject, from biological information acquired by a biological information acquisition unit. A recovery amount calculation unit calculates the amount of recovery, which is the amount of physical activity recovered by the subject, from the biological information acquired by the biological information acquisition unit. A retained physical activity amount calculation unit calculates the amount of retained physical activity, which is the amount of physical activity retained by the subject, from the reference amount of physical activity set by the reference physical activity amount setting unit, the consumption amount of physical activity calculated by the physical activity consumption amount calculation unit, and the amount of recovery calculated by the recovery amount calculation unit. Therefore, the amount of physical activity retained by the subject can be calculated instantaneously.

17 Claims, 13 Drawing Sheets

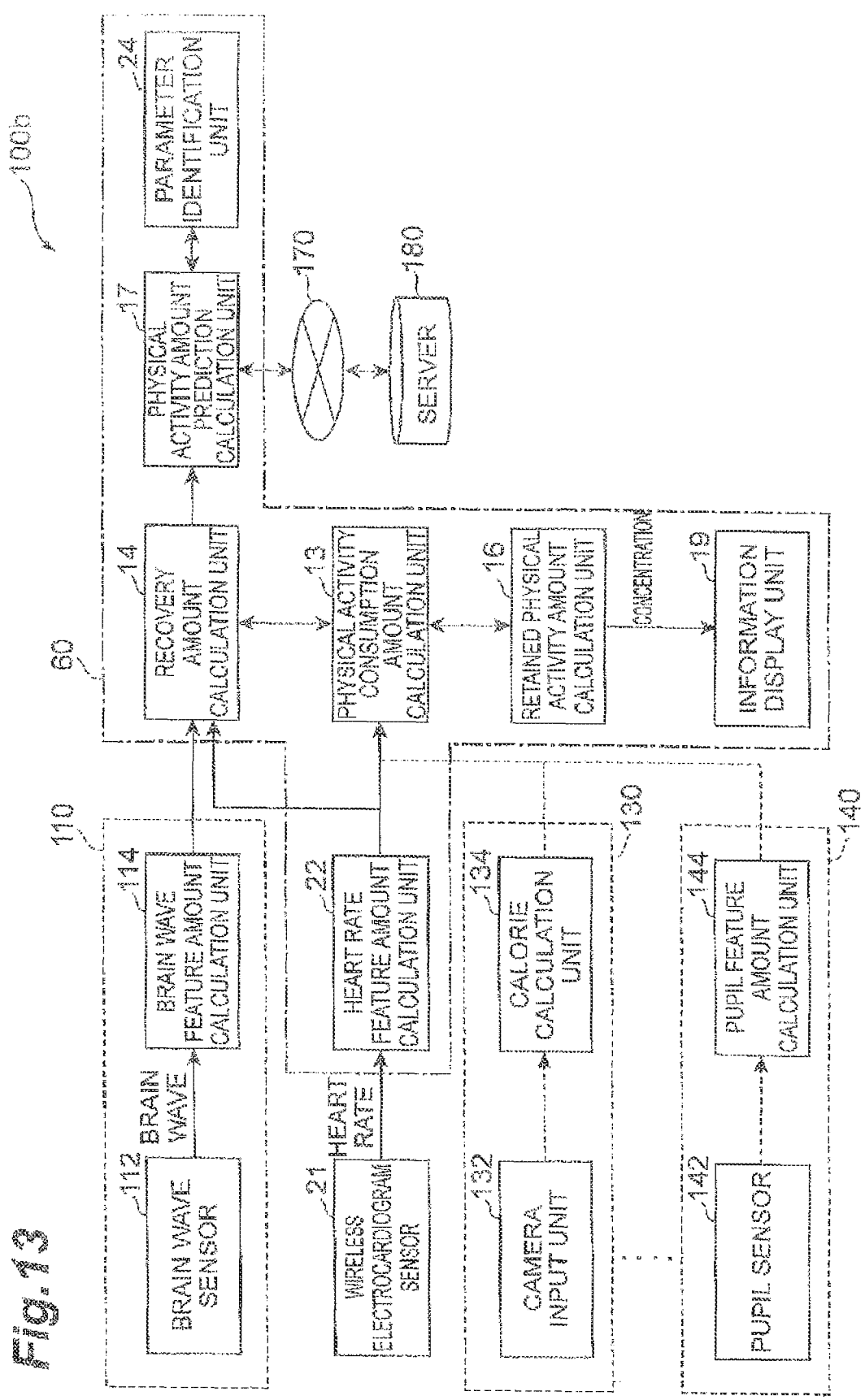

DEVICE FOR CALCULATING AMOUNT OF RETAINED PHYSICAL ACTIVITY, METHOD FOR CALCULATING AMOUNT OF RETAINED PHYSICAL ACTIVITY AND SYSTEM FOR CALCULATING AMOUNT OF RETAINED PHYSICAL ACTIVITY

CROSS REFERENCE TO RELATED APPLICATIONS

This application is a National Stage of International Application No. PCT/JP2012/061428 filed Apr. 27, 2012, the contents of all of which are incorporated herein by reference in their entirety.

TECHNICAL FIELD

An embodiment of the present invention relates to a device for calculating the amount of retained physical activity, a method for calculating the amount of retained physical activity, and a system for calculating the amount of retained physical activity, and relates to a device for calculating the amount of retained physical activity, a method for calculating the amount of retained physical activity, and a system for calculating the amount of retained physical activity that calculates the amount of physical activity retained by a subject.

BACKGROUND ART

Devices for managing the health of humans have been proposed. For example, Patent Literature 1 discloses a health management device that calculates the degree of fatigue in a day from the exercise time and the sleep time of a subject. The device disclosed in Patent Literature 1 selects exercise or sleep based on the degree of influence of exercise time and sleep time on the degree of fatigue, and provides advice to improve either to the subject.

CITATION LIST

Patent Literature

[Patent Literature 1] Japanese Unexamined Patent Application Publication No. 2007-222276

SUMMARY OF INVENTION

Technical Problem

However, since the technique described above is only to calculate the degree of fatigue in a day simply from the exercise time and the sleep time of a subject, the amount of physical activity retained by the subject (limit of physical activity of the subject) cannot be calculated instantaneously. An embodiment of the present invention has been made in view of such circumstances, and the object is to provide a device for calculating the amount of retained physical activity, a method for calculating the amount of retained physical activity, and a system for calculating the amount of retained physical activity that can calculate the amount of physical activity retained by the subject instantaneously.

Solution to Problem

An embodiment of the present invention is a device for calculating an amount of retained physical activity including: a reference physical activity amount setting unit that sets a reference amount of physical activity that is a reference of an amount of physical activity of a subject; a biological information acquisition unit that acquires biological information of the subject; a physical activity consumption amount calculation unit that calculates a consumption amount of physical activity, which is the amount of physical activity consumed by the subject, from the biological information acquired by the biological information acquisition unit; a recovery amount calculation unit that calculates an amount of recovery, which is the amount of physical activity recovered by the subject, from the biological information acquired by the biological information acquisition unit; and a retained physical activity amount calculation unit that calculates an amount of retained physical activity, which is the amount of physical activity retained by the subject, from the reference amount of physical activity set by the reference physical activity amount setting unit, the consumption amount of physical activity calculated by the physical activity consumption amount calculation unit, and the amount of recovery calculated by the recovery amount calculation unit.

According to this configuration, the physical activity consumption amount calculation unit calculates the consumption amount of physical activity, which is the amount of physical activity consumed by the subject, from the biological information acquired by the biological information acquisition unit. The recovery amount calculation unit calculates the amount of recovery, which is the amount of physical activity recovered by the subject, from the biological information acquired by the biological information acquisition unit. The retained physical activity amount calculation unit calculates the amount of retained physical activity, which is the amount of physical activity retained by the subject, from the reference amount of physical activity set by the reference physical activity amount setting unit, the consumption amount of physical activity calculated by the physical activity consumption amount calculation unit, and the amount of recovery calculated by the recovery amount calculation unit. Therefore, the amount of physical activity retained by the subject can be calculated instantaneously.

In this case, the recovery amount calculation unit can determine that the subject is in a sleep state from the biological information acquired by the biological information acquisition unit, and calculates the amount of recovery based on the biological information in the sleep state.

According to this configuration, the recovery amount calculation unit determines that the subject is in a sleep state from the biological information acquired by the biological information acquisition unit, and calculates the amount of recovery based on the biological information in the sleep state. Therefore, it is possible to calculate the amount of recovery based on the biological information in a sleep state that is closely related with the recovery of the amount of physical activity of the subject.

In this case, the recovery amount calculation unit can calculate the amount of recovery based on either sleep spindles or $\theta$ waves of brain waves of the biological information in the sleep state.

According to this configuration, the recovery amount calculation unit calculates the amount of recovery based on either sleep spindles or $\theta$ waves of brain waves of the biological information in the sleep state. Therefore, even if the amount of recovery cannot be calculated from the depth of sleep, it is possible to calculate the amount of recovery.

In addition, the recovery amount calculation unit can calculate the amount of recovery based on a depth of sleep of the subject estimated from the biological information in the sleep state.

According to this configuration, the recovery amount calculation unit calculates the amount of recovery based on the depth of sleep of the subject estimated from the biological information in the sleep state. Therefore, even if the degree of recovery cannot be calculated with the cumulative time of appearance of θ waves or the like as in a case where the subject is an elderly person, it is possible to calculate the amount of recovery.

In addition, the reference physical activity amount setting unit can set the amount of retained physical activity, which has been calculated immediately before by the retained physical activity amount calculation unit, as the reference amount of physical activity.

According to this configuration, the reference physical activity amount setting unit sets the amount of retained physical activity, which has been calculated immediately before by the retained physical activity amount calculation unit, as the reference amount of physical activity. Therefore, the amount of retained physical activity of the subject that changes instantaneously can be calculated more accurately.

In addition, the retained physical activity amount calculation unit can correct a parameter for calculating the amount of retained physical activity based on history of the consumption amount of physical activity and the amount of recovery of the subject from the past.

According to this configuration, the retained physical activity amount calculation unit corrects parameters for calculating the amount of retained physical activity based on the history of the consumption amount of physical activity and the amount of recovery of the subject from the past. Therefore, it is possible to calculate the amount of physical activity that closer reflects the circumstances of the subject.

In addition, it is possible to further include a display unit that displays the amount of retained physical activity calculated by the retained physical activity amount calculation unit.

According to this configuration, the display unit displays the amount of retained physical activity calculated by the retained physical activity amount calculation unit. Therefore, the amount of physical activity retained by the subject can be displayed instantaneously.

In addition, it is possible to further include a notification unit that, when the amount of retained physical activity calculated by the retained physical activity amount calculation unit becomes equal to or less than a predetermined value, notifies that the amount of retained physical activity has become equal to or less than the predetermined value.

According to this configuration, when the amount of retained physical activity calculated by the retained physical activity amount calculation unit becomes equal to or less than a predetermined value, the notification unit notifies that the amount of retained physical activity has become equal to or less than the predetermined value. Therefore, it is possible to immediately see that the amount of physical activity retained by the subject has been reduced.

In addition, an embodiment of the present invention is a method for calculating an amount of retained physical activity including: a reference physical activity amount setting step of setting a reference amount of physical activity that is a reference of an amount of physical activity of a subject; a biological information acquisition step of acquiring biological information of the subject; a physical activity consumption amount calculation step of calculating a consumption amount of physical activity, which is the amount of physical activity consumed by the subject, from the biological information acquired in the biological information acquisition step; a recovery amount calculation step of calculating an amount of recovery, which is the amount of physical activity recovered by the subject, from the biological information acquired in the biological information acquisition step; and a retained physical activity amount calculation step of calculating an amount of retained physical activity, which is the amount of physical activity retained by the subject, from the reference amount of physical activity set in the reference physical activity amount setting step, the consumption amount of physical activity calculated in the physical activity consumption amount calculation step, and the amount of recovery calculated in the recovery amount calculation step.

In addition, an embodiment of the present invention is a system for calculating an amount of retained physical activity including: a reference physical activity amount setting unit that sets a reference amount of physical activity that is a reference of an amount of physical activity of a subject; a biological information acquisition unit that acquires biological information of the subject; a physical activity consumption amount calculation unit that calculates a consumption amount of physical activity, which is the amount of physical activity consumed by the subject, from the biological information acquired by the biological information acquisition unit; a recovery amount calculation unit that calculates an amount of recovery, which is the amount of physical activity recovered by the subject, from the biological information acquired by the biological information acquisition unit; and a retained physical activity amount calculation unit that calculates an amount of retained physical activity, which is the amount of physical activity retained by the subject, from the reference amount of physical activity set by the reference physical activity amount setting unit, the consumption amount of physical activity calculated by the physical activity consumption amount calculation unit, and the amount of recovery calculated by the recovery amount calculation unit.

In the system for calculating the amount of retained physical activity of the embodiment of the present invention, the reference physical activity amount setting unit, the biological information acquisition unit, the physical activity consumption amount calculation unit, the recovery amount calculation unit, and the retained physical activity amount calculation unit do not necessarily need to be one device, and these units may be separately present.

Advantageous Effects of Invention

According to the device for calculating the amount of retained physical activity, the method for calculating the amount of retained physical activity, and the system for calculating the amount of retained physical activity of the embodiments of the present invention, it is possible to calculate the amount of physical activity retained by the subject instantaneously.

BRIEF DESCRIPTION OF DRAWINGS

FIG. 13 is a block diagram showing a biological activity amount management system according to a third embodiment.

DESCRIPTION OF EMBODIMENTS

Figure 1:
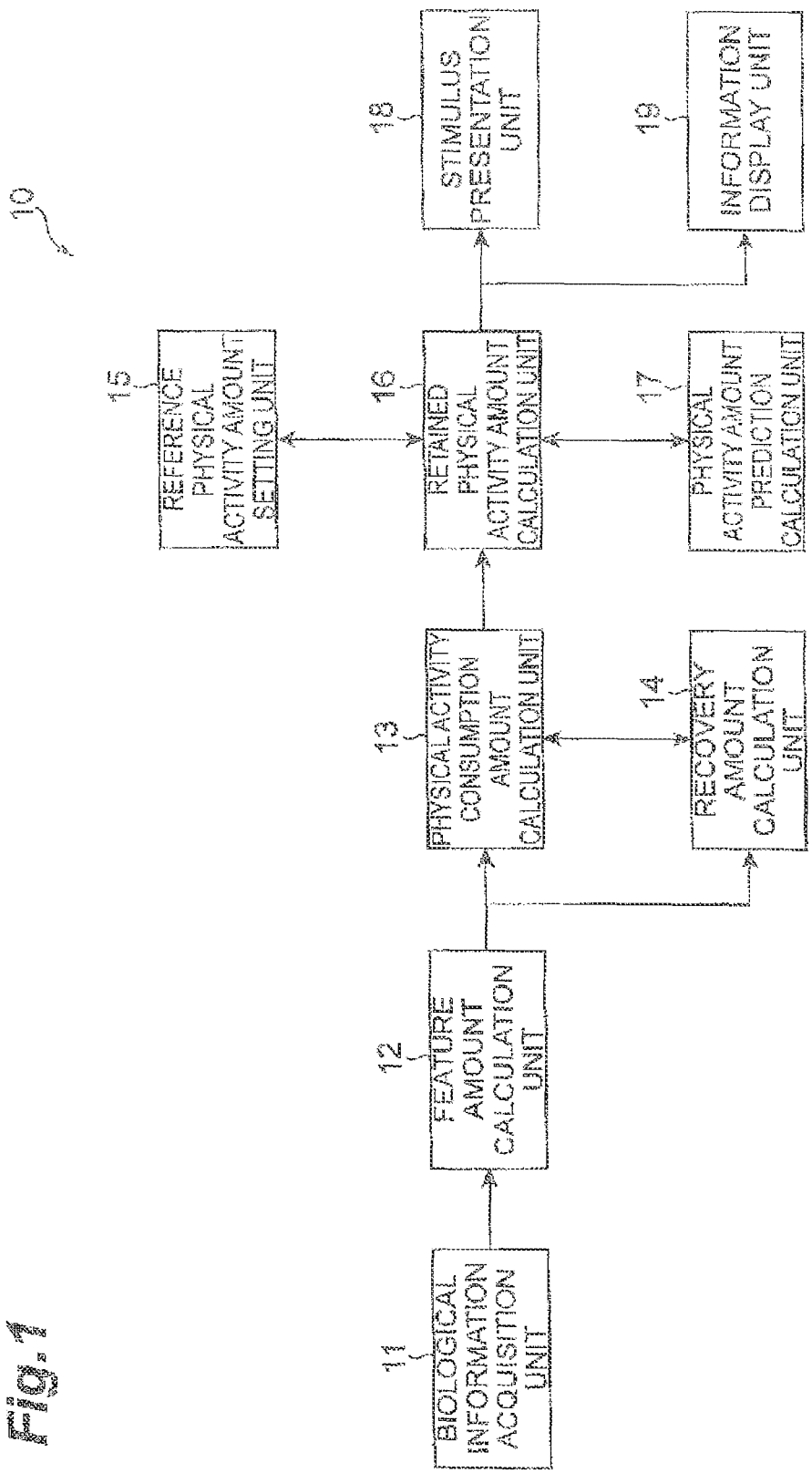
FIG. 1 is a block diagram showing the configuration of a biological activity amount management device according to a first embodiment.

Hereinafter, an embodiment of the present invention will be described with reference to the accompanying diagrams. As shown in FIG. 1, a biological activity amount management device 10 according to a first embodiment of the present invention includes a biological information acquisition 11, a feature amount calculation unit 12, a physical activity consumption amount calculation unit 13, a recovery amount calculation unit 14, a reference physical activity amount setting unit 15, a retained physical activity amount calculation unit 16, a physical activity amount prediction calculation unit 17, a stimulus presentation unit 18, and an information display unit 19. The biological activity amount management device 10 of the present embodiment is configured as a mobile terminal owned by the subject. Alternatively, the biological activity amount management device 10 of the present embodiment is configured as a device that is installed in vehicles, accommodations, medical institutions, ordinary homes, and the like.

The biological information acquisition unit 11 acquires biological information of the subject. As the biological information of the subject, the biological information acquisition unit 11 acquires at least one or more physiological indicators including a heart rate required to estimate the state of the subject, a heartbeat such as a pulse wave, breathing, a brain wave, and body movement of the subject measured by an acceleration sensor or the like. The method for acquiring the biological information may be either by contact or by non-contact. For example, the biological information acquisition unit 11 can be a piezoelectric element, an acceleration sensor, or a physiological indicator detecting device provided in the steering wheel or seat of the vehicle. The biological information acquisition unit 11 can measure brain waves as the biological information of the subject in order to improve the accuracy of estimation of the state of the subject. Therefore, the biological information acquisition unit 11 does not need to detect the brain waves constantly. The biological information acquisition unit 11 detects the brain waves of the subject at one or more places. The biological information acquisition unit 11 can measure acceleration in order to improve the accuracy of estimation of the amount of physical activity due to exercise of the subject or to measure the heart rate or breathing.

The feature amount calculation unit 12 calculates a feature amount, which is required for the estimation of the amount of physical activity of the subject, from the biological information acquired by the biological information acquisition unit 11. The feature amount calculation unit 12 may calculate whether or not acceleration as a feature amount exceeds a predetermined threshold value, and the physical activity consumption amount calculation unit 13 may estimate the movement state and exercise state of the subject from the feature amount. The feature amount calculation unit 12 may calculate a variance, a standard deviation, and a coefficient of variation of the heartbeat interval as feature amounts of the heartbeat fluctuation. The feature amount calculation unit 12 may calculate the feature amount of the heartbeat fluctuation by performing frequency conversion of the heartbeat interval per unit time. The feature amount calculation unit 12 may calculate the degree of concentration of the subject, as a feature amount, from the brain waves or the heart rate of the subject.

The physical activity consumption amount calculation unit 13 calculates the consumption amount of physical activity, which is the amount of physical activity of the subject that is consumed at each point in time in a day, from the feature amount of the heart rate and the feature amount of brain waves that have been calculated by the feature amount calculation unit 12. The physical activity consumption amount calculation unit 13 can calculate the consumption amount of physical activity of the subject using a human state estimation equation that is a polynomial having the above-described feature amounts as parameters. Therefore, the physical activity consumption amount calculation unit 13 can calculate the consumption amount of physical activity of the subject as consecutive values. In addition, the physical activity consumption amount calculation unit 13 can also estimate the mental load of the subject by calculating the consumption amount of physical activity using the feature amount of the heart rate and the feature amount of brain waves.

The recovery amount calculation unit 14 calculates the amount of recovery, which is the amount of physical activity of the subject recovered at each point in time in a day, from the feature amount of the heart rate and the feature amount of brain waves that have been calculated by the feature amount calculation unit 12. The recovery amount calculation unit 14 can calculate the amount of recovery from the percentage of REM sleep, the cumulative time of appearance of θ waves, and the number or density of sleep spindles or θ waves. The recovery amount calculation unit 14 can calculate the amount of recovery by the four fundamental arithmetic operations on the plurality of feature amounts described above. Therefore, the recovery amount calculation unit 14 can calculate the amount of recovery regardless of the age of the subject.

The reference physical activity amount setting unit 15 sets the reference amount of physical activity that is a reference of the amount of physical activity of the subject. The reference physical activity amount setting unit 15 can set the amount of retained physical activity, which is the remaining amount of physical activity retained by the subject in a previous day or from the past, as the reference amount of physical activity that is an initial value. The reference physical activity amount setting unit 15 can reset the reference amount of physical activity on a daily basis. The reference physical activity amount setting unit 15 can set the amount of retained physical activity, which has been currently calculated by the retained physical activity amount calculation unit 16, as the reference amount of physical activity.

The retained physical activity amount calculation unit 16 calculates the amount of retained physical activity, which is the remaining amount of physical activity that the subject retains, from the reference amount of physical activity set by the reference physical activity amount setting unit 15, the consumption amount of physical activity calculated by the physical activity consumption amount calculation unit 13, and the amount of recovery calculated by the recovery amount calculation unit 14.

The physical activity amount prediction calculation unit 17 has a database in which information regarding the consumption amount of physical activity and the amount of recovery of the subject from the past is stored. The physical activity amount prediction calculation unit 17 calculates a change in the amount of retained physical activity of the subject in a day from the information regarding the consumption amount of physical activity and the amount of recovery of the subject from the past. Therefore, in the present embodiment, it is possible to check for a change in the state of each subject and send a notification before reaching the limit of the physical activity of the subject.

The stimulus presentation unit 18 presents a stimulus to maintain or improve the concentration of the subject when the amount of retained physical activity calculated by the retained physical activity amount calculation unit 16 becomes equal to or less than a predetermined threshold value, or when the amount of change in the amount of retained physical activity calculated by the retained physical activity amount calculation unit 16 becomes equal to or greater than a predetermined threshold value, or when the degree of concentration or the consumption amount of physical activity of the subject calculated by the feature amount calculation unit 12 and the physical activity consumption amount calculation unit 13 becomes equal to or less than a predetermined threshold value, or when the amount of change in the degree of concentration or the consumption amount of physical activity of the subject calculated by the feature amount calculation unit 12 and the physical activity consumption amount calculation unit 13 becomes equal to or greater than a predetermined threshold value. The stimulus presentation unit 18 may have a map of the method of presentation of a stimulus corresponding to each state of the subject. For example, the stimulus presentation unit 18 can present a physical stimulus, such as light, sound, vibration, heat, cold air, smell, and an image, to the subject.

The information display unit 19 displays the transition of the amount of retained physical activity calculated by the retained physical activity amount calculation unit 16 or the transition of the amount of retained physical activity of the subject in a day calculated by the physical activity amount prediction calculation unit 17 for the subject. The information display unit 19 can propose a schedule of rest or work according to the remaining amount of retained physical activity that is retained by the subject.

Figure 2:
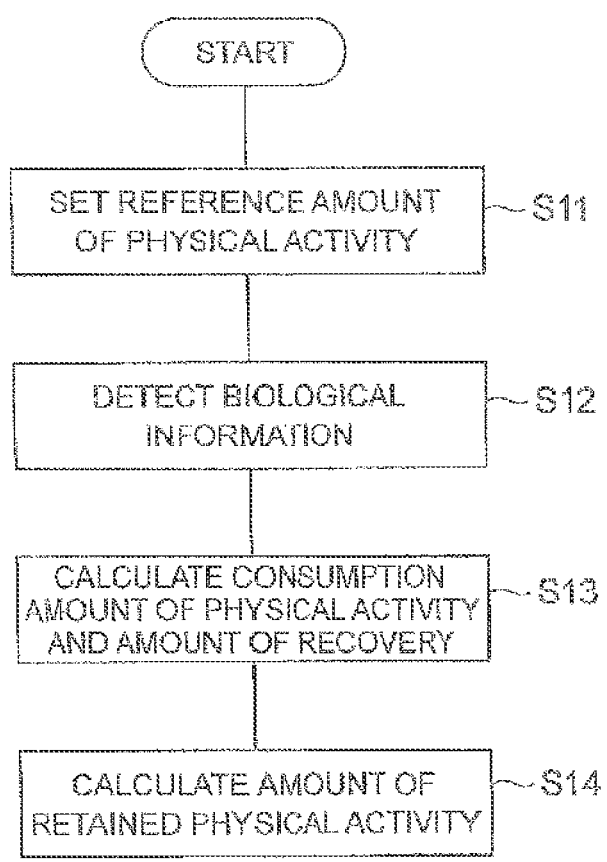
FIG. 2 is a flowchart showing the operation of the biological activity amount management device according to the first embodiment.

Hereinafter, the operation of the biological activity amount management device 10 of the present embodiment will be described. As shown in FIG. 2, the reference physical activity amount setting unit 15 of the biological activity amount management device 10 sets the reference amount of physical activity (S11). The biological information acquisition unit 11 of the biological activity amount management device 10 acquires biological information of the subject (S12). The physical activity consumption amount calculation unit 13 of the biological activity amount management device 10 calculates the consumption amount of physical activity of the subject, and the recovery amount calculation unit 14 of the biological activity amount management device 10 calculates the amount of recovery of the subject (S13). The retained physical activity amount calculation unit 16 of the biological activity amount management device calculates the amount of retained physical activity (S14). According to the calculated amount of retained physical activity, when the amount of retained physical activity becomes equal to or less than a predetermined value, the stimulus presentation unit 18 presents the situation to the subject by stimulus presentation that the amount of retained physical activity has become equal to or less than the predetermined value. The information display unit 19 displays the current remaining amount of retained physical activity instantaneously for the subject. In addition, the setting of the reference amount of physical activity (S11) may be performed either after the acquisition of biological information (S12) or after the calculation of the consumption amount of physical activity and the amount of recovery (S13).

The calculation of the consumption amount of physical activity of the subject by the physical activity consumption amount calculation unit 13 will be described. The biological information acquisition unit 11 acquires biological information such as brain waves, heart rate, breathing, or other activity indicators of the subject. The feature amount calculation unit 12 calculates a feature amount from the biological information acquired by the biological information acquisition unit 11. Based on the feature amount calculated by the feature amount calculation unit 12, the physical activity consumption amount calculation unit 13 calculates the consumption amount of physical activity.

In the present embodiment, the physical activity consumption amount calculation unit 13 can calculate the consumption amount of physical activity due to the degree of concentration of the subject being low. The degree of concentration of the subject can be determined from the reaction speed of the subject with respect to the light stimulus, the result of an answer to a calculation question or the like, or the result of a game, for example. The degree of concentration after the subject wakes up from 7 to 8 hours of sleep can be set to the initial value of the degree of concentration of the subject. In addition, the initial value of the degree of concentration of the subject can be determined from information, such as age or sex specifying each subject, by referring to a predetermined database. In addition, the average value of the degree of concentration of the subject over several normal days can be set as the initial value of the degree of concentration of the subject.

The degree of concentration of the subject does not necessarily need to be calculated by making the subject answer a question or the like. It is known that lack of sleep and reaction time with respect to the light stimulus are in a linear relationship and the reaction time reflects the fatigue of the subject. The present inventor has elucidated that there is a correlation among the brain activity indicating the mental activity, the subjectivity of the subject for the consumption amount of physical activity (fatigue), and the reaction time. The present inventor has determined that there is a possibility that the consumption amount of physical activity by mental activity and the amount of recovery by sleep can be centralized.

Figure 3:
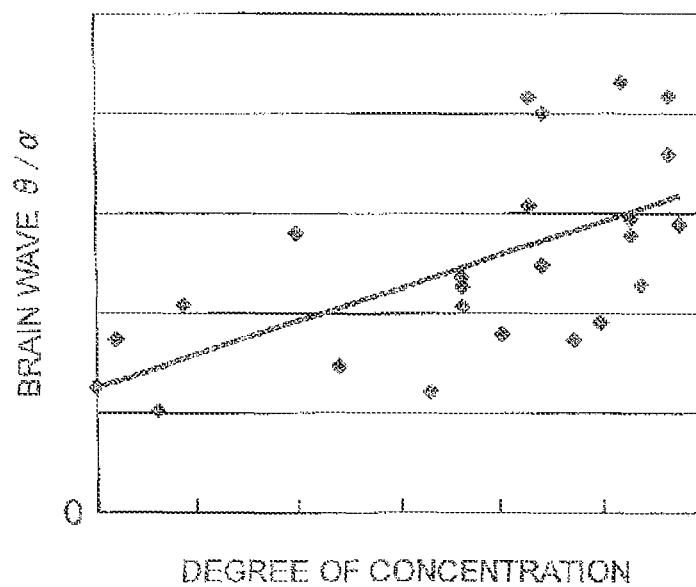
FIG. 3 is a graph showing the relationship between the degree of concentration and the θ wave.
Figure 4:
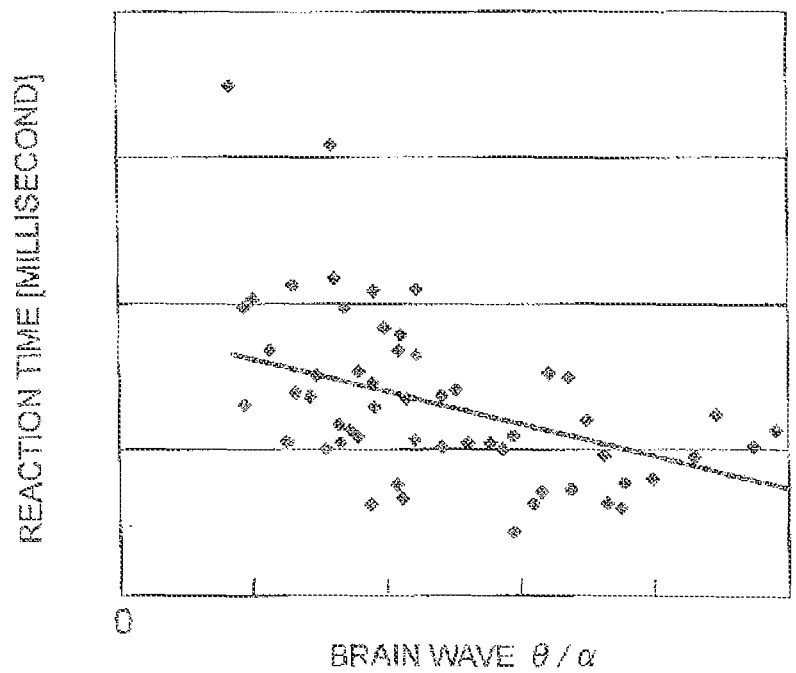
FIG. 4 is a graph showing the relationship between the θ wave and reaction time.
Figure 5:
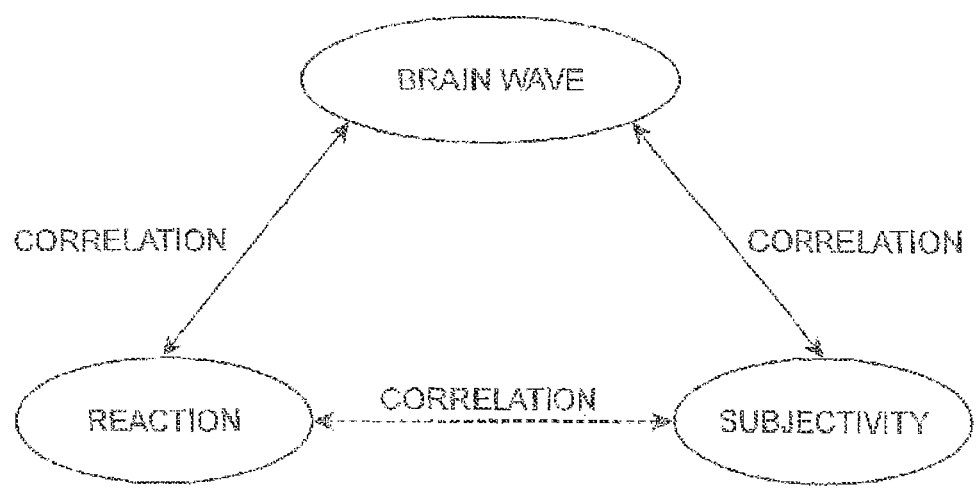
FIG. 5 is a diagram showing the correlation among subjectivity, a brain wave, and a response.

As shown in FIG. 3, as the degree of concentration of the subject increases, the ratio of θ waves to α waves of brain waves increases linearly. In addition, in order to reduce the difference between subjects, the vertical axis in the graph of FIG. 3 indicates a value obtained by dividing the amount of θ waves by the amount of α waves. In addition, as shown in FIG. 4, as the ratio of θ waves to α waves of brain waves increases, the reaction time of the subject with respect to the light stimulus or the like decreases linearly. Accordingly, as shown in FIG. 5, it is thought that there is a correlation between the subjective degree of concentration of the subject and the brain waves and there is a correlation between the brain waves and the response of the subject, and accordingly, there is a correlation between the subjective degree of concentration of the subject and the response of the subject. Therefore, in the present embodiment, the consumption amount of physical activity of the subject, the degree of concentration of the subject, or the mental load of the subject can also be calculated based on the feature amount of the brain waves.

In the present embodiment, since the consumption amount of physical activity can be calculated due to the degree of concentration of the subject being low, it is possible to calculate the intensity of the load on the subject that cannot be calculated with only the exercise time as disclosed in Patent Literature 1. In the present embodiment, it is possible to calculate the consumption amount of physical activity and the amount of retained physical activity of the subject from the concentration, relaxation, drowsiness, recovery, wake-up, sleep state, and the like of a human in a day.

Figure 6:
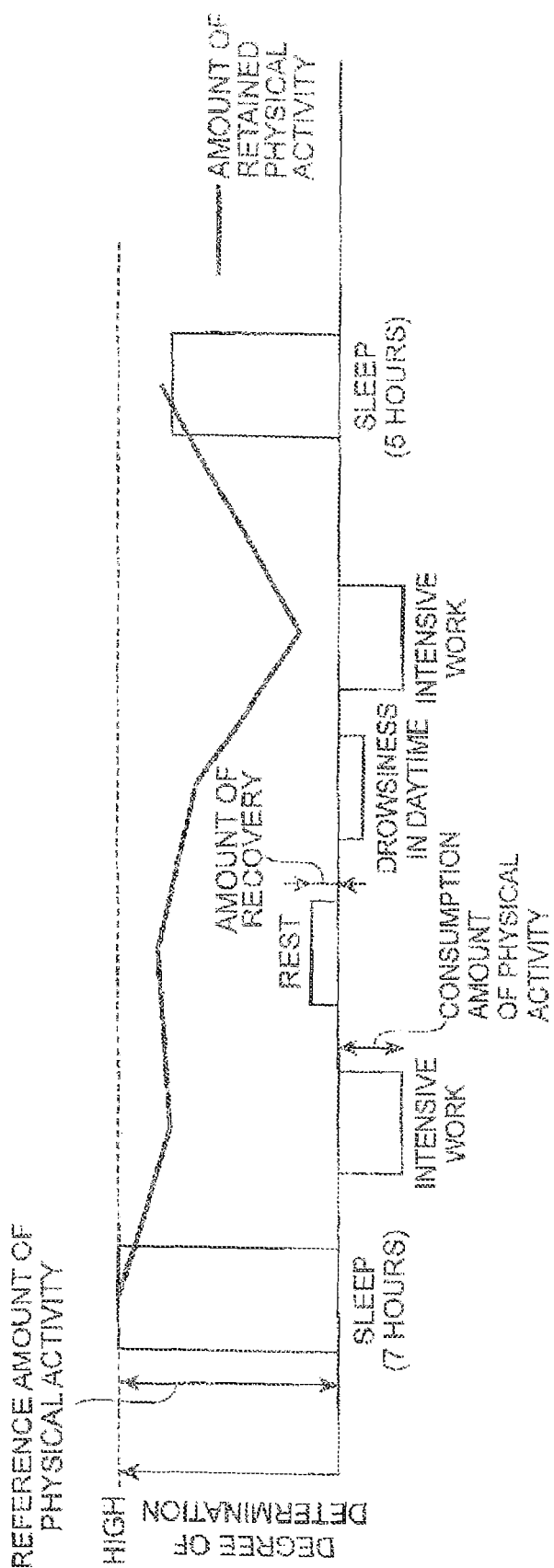
FIG. 6 is a graph showing a change in the amount of retained physical activity in a day.

Therefore, in the present embodiment, as shown in FIG. 6, it is possible to show the change in the amount of retained physical activity by centralizing and visualizing the amount of retained physical activity, the consumption amount of physical activity, and the amount of recovery of the subject. For this reason, when the amount of retained physical activity is reduced due to intensive work, it is possible to indicate the amount the subject can further work. Alternatively, when the consumption amount of physical activity comparable to the day is expected as that of the next day, it is possible to indicate the amount of recovery that will be required by how much sleep time at the time of sleep after intensive work.

Next, the calculation of the amount of recovery of the subject by the recovery amount calculation unit 14 will be described. Similar to the physical activity consumption amount calculation unit 13, the feature amount calculation unit 12 calculates a feature amount from the biological information acquired by the biological information acquisition unit 11, and the recovery amount calculation unit 14 calculates the amount of recovery based on the feature amount calculated by the feature amount calculation unit 12.

In the present embodiment, the recovery amount calculation unit 14 can calculate the amount of recovery from the depth of sleep of the subject during sleep. Whether or not the subject is in a sleep state or the depth of sleep of the subject can be calculated from any of the feature amounts, such as a heart rate or breathing. In addition, the recovery amount calculation unit 14 can calculate the depth of sleep of the biorhythm model from the body movement of the subject.

Figure 7:
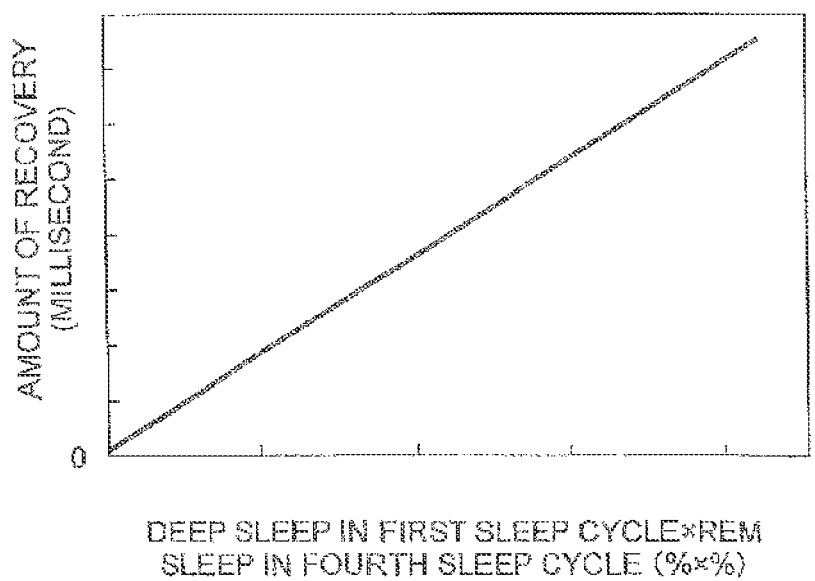
FIG. 7 is a graph showing the relationship between the amount of recovery and a product between the percentage of deep sleep (sleep stage 4) in the first sleep cycle and the percentage of REM sleep in the fourth sleep cycle.

In the present embodiment, the recovery amount calculation unit 14 can calculate the amount of recovery from the multiplication of deep sleep equivalent to the sleep stage 4 and the percentage of REM sleep or the cumulative time of REM sleep. For example, as shown in FIG. 7, as a product between the percentage of deep sleep (sleep stage 4) in the first sleep cycle and the percentage of REM sleep in the fourth sleep cycle increases, the amount of recovery also increases linearly. Therefore, the recovery amount calculation unit 14 can calculate the amount of recovery from the product between the percentage of deep sleep (sleep stage 4) in the first sleep cycle and the percentage of REM sleep in the fourth sleep cycle.

It is known that the reaction time is delayed if non-REM sleep is insufficient. However, the percentage of REM sleep and the amount of θ waves are reduced if the age of the subject is over 40, and the θ wave is not likely to appear if the age of the subject is over 60. Accordingly, if the subject is an elderly person, it is not possible to calculate the amount of recovery with only the cumulative amount of θ waves or the like. In the present embodiment, however, it is possible to calculate the amount of recovery by the percentage of REM sleep.

On the other hand, in the present embodiment, the recovery amount calculation unit 14 can calculate the amount of recovery from the brain waves of the subject during sleep. Since the percentage of non-REM sleep decreases with the age of the subject as described above, the exact calculation of the amount of recovery according to the age of the subject may be difficult in the above-described method. Therefore, the recovery amount calculation unit 14 can calculate the amount of recovery, for example, from the number or density of sleep spindles or θ waves as the feature amount of brain waves of the subject.

Figure 8:
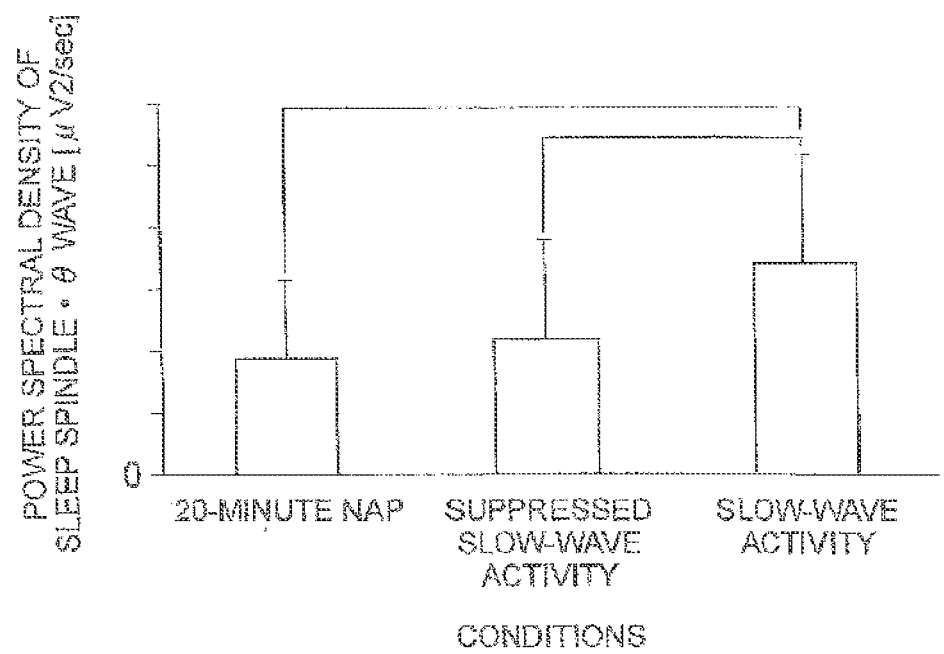
FIG. 8 is a graph showing the power spectral density of θ waves or sleep spindles with respect to each condition of a 20-minute nap, suppressed slow-wave activity, and slow-wave activity.
Figure 9:
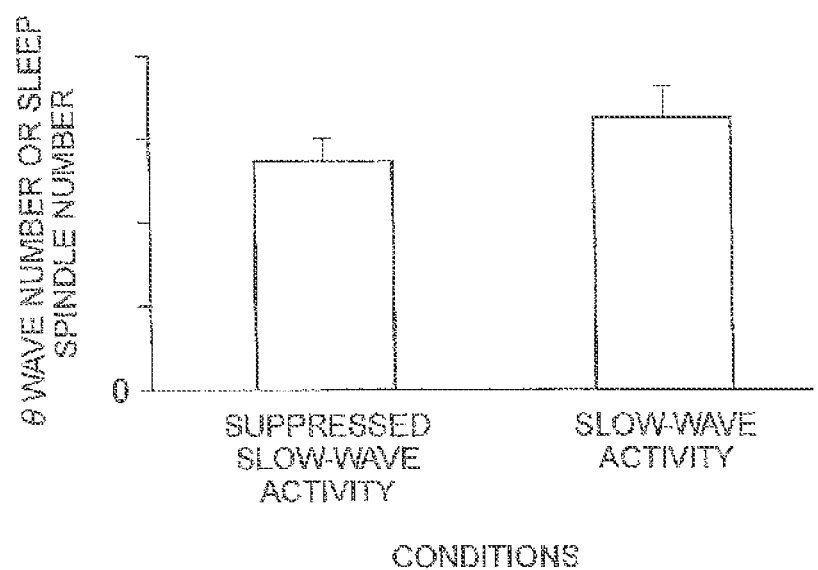
FIG. 9 is a graph showing the θ wave number or the sleep spindle number with respect to each condition of suppressed slow-wave activity and slow-wave activity.
Figure 10:
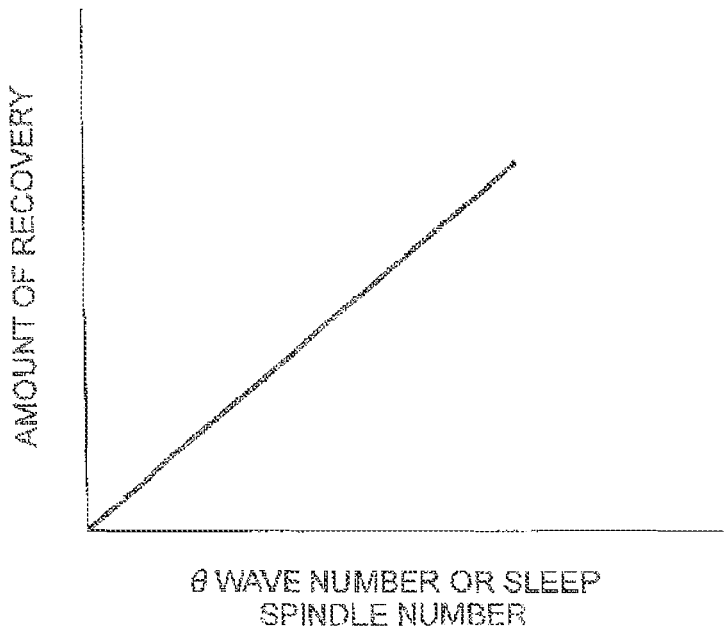
FIG. 10 is a graph showing the relationship between the θ wave number or the sleep spindle number and the amount of recovery.

As shown in FIG. 8, it can be seen that the power spectral density of sleep spindles or θ waves in slow-wave activity of sleep that is not suppressed is larger than the power spectral density of sleep spindles or θ waves in slow-wave activity suppressed by the stimulus given to the subject or the power spectral density of sleep spindles or θ waves in a short nap of 20 minutes. On the other hand, FIG. 9 shows that there is no significant difference between the number of θ waves or sleep spindles in slow-wave activity that is suppressed and the number of θ waves or sleep spindles in slow-wave activity that is not suppressed. In addition, as shown in FIG. 10, it can also be seen that the amount of recovery increases linearly as the number of θ waves or sleep spindles increases. Accordingly, even if the depth of sleep cannot be detected, the recovery amount calculation unit 14 can calculate the amount of recovery of the subject from the number of θ waves or sleep spindles.

Sleep spindles or θ waves can be directly calculated from the brain waves of the subject. Sleep spindles or θ waves can be detected by any of frequency analysis, wavelet analysis, waveform recognition method, and the like. If it is not possible to detect the brain waves of the subject, sleep spindles or θ waves can be calculated from the elapsed time of the sleep stage 2 of the subject.

The retained physical activity amount calculation unit 16 calculates the amount of retained physical activity of the subject by substituting the parameters obtained by measurement into the state equation (amount of retained physical activity=$a_1$×reference amount of physical activity−$a_2$×consumption amount of physical activity+$a_3$×amount of recovery), for example. $a_1$ to $a_3$ are arbitrary correction coefficients. These correction coefficients can be set and changed from the history of the consumption amount of physical activity and the amount of recovery of the subject from the past.

According to the present embodiment, the physical activity consumption amount calculation unit 13 calculates the consumption amount of physical activity, which is the amount of physical activity consumed by the subject, from the biological information acquired by the biological information acquisition unit 11. The recovery amount calculation unit 14 calculates the amount of recovery, which is the amount of physical activity recovered by the subject, from the biological information acquired by the biological information acquisition unit 11. The retained physical activity amount calculation unit 16 calculates the amount of retained physical activity, which is the amount of physical activity retained by the subject, from the reference amount of physical activity set by the reference physical activity amount setting unit 15, the consumption amount of physical activity calculated by the physical activity consumption amount calculation unit 13, and the amount of recovery calculated by the recovery amount calculation unit 14. Therefore, the amount of physical activity retained by the subject can be calculated instantaneously.

According to the present embodiment, the recovery amount calculation unit 14 determines that the subject is in a sleep state from the biological information acquired by the biological information acquisition unit 11, and calculates the amount of recovery based on the biological information in the sleep state. Therefore, it is possible to calculate the amount of recovery based on the biological information in a sleep state that is closely related with the recovery of the amount of physical activity of the subject.

According to the present embodiment, the recovery amount calculation unit 14 calculates the amount of recovery based on either sleep spindles or θ waves of the brain waves of the biological information in a sleep state. Therefore, even if the amount of recovery cannot be calculated from the depth of sleep, it is possible to calculate the amount of recovery.

According to the present embodiment, the recovery amount calculation unit 14 calculates the amount of recovery based on the depth of sleep of the subject estimated from the biological information in a sleep state. Therefore, even if the degree of recovery cannot be calculated with the cumulative time of appearance of θ waves or the like as in a case where the subject is an elderly person, it is possible to calculate the amount of recovery.

According to the present embodiment, the reference physical activity amount setting unit 15 sets the amount of retained physical activity, which has been calculated immediately before by the retained physical activity amount calculation unit 16, as the reference amount of physical activity. Therefore, the amount of retained physical activity of the subject that changes instantaneously can be calculated more accurately.

According to the present embodiment, the retained physical activity amount calculation unit 16 corrects parameters for calculating the amount of retained physical activity based on the history of the consumption amount of physical activity and the amount of recovery of the subject from the past. Therefore, it is possible to calculate the amount of physical activity that closer reflects the circumstances of the subject.

According to the present embodiment, the information display unit 19 displays the amount of retained physical activity calculated by the retained physical activity amount calculation unit 16. Therefore, the amount of physical activity retained by the subject can be displayed instantaneously.

According to the present embodiment, when the information display unit 19 displays that the amount of retained physical activity calculated by the retained physical activity amount calculation unit 16 has become equal to or less than a predetermined threshold value, the stimulus presentation unit 18 presents a stimulus to maintain or improve the concentration of the subject. Therefore, it is possible to immediately notify that the amount of physical activity retained by the subject has been reduced while maintaining or improving the concentration of the subject.

Figure 11:
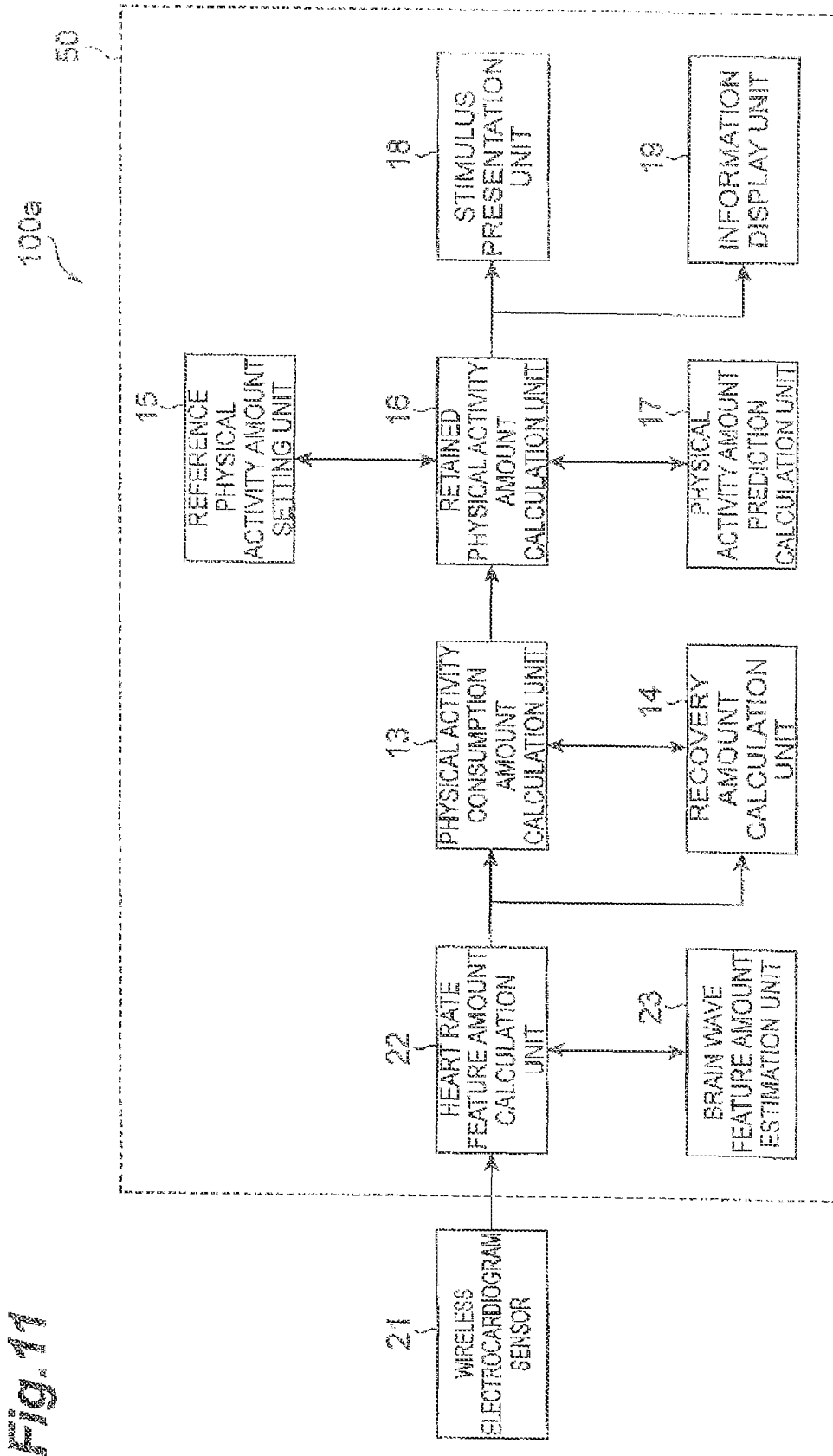
FIG. 11 is a block diagram showing a biological activity amount management system according to a second embodiment.

Hereinafter, a second embodiment of the present invention will be described. Although the respective components for calculating the amount of retained physical activity of the subject are provided in one device in the first embodiment described above, a system of the present embodiment is configured such that the respective components for calculating the amount of retained physical activity of the subject are separately provided in a plurality of units. As shown in FIG. 11, a system for calculating the amount of retained physical activity 100a of the present embodiment includes a wireless electrocardiogram sensor 21 and a mobile terminal 50.

The wireless electrocardiogram sensor 21 is attached to the chest of the subject using disposable electrodes. The wireless electrocardiogram sensor 21 measures the electrocardiogram of the subject, and transmits the measurement result to the mobile terminal 50 by short-distance wireless communication, such as normal wireless communication or bluetooth (registered trademark).

The mobile terminal 50 is a mobile phone, a wrist watch, a mobile personal computer, or the like that a subject or a person associated with the subject, such as a relative of the subject, carries. The mobile terminal 50 includes a heart rate feature amount calculation unit 22 and a brain wave feature amount estimation unit 23 in addition to the physical activity consumption amount calculation unit 13, the recovery amount calculation unit 14, the reference physical activity amount setting unit 15, the retained physical activity amount calculation unit 16, the physical activity amount prediction calculation unit 17, the stimulus presentation unit 18, and the information display unit 19 of the biological activity amount management device 10 of the first embodiment described above.

The heart rate feature amount calculation unit 22 calculates a heart rate HR from the interval (RRI) of R waves in the information regarding the electrocardiogram of the subject measured by the wireless electrocardiogram sensor 21, and calculates a variance RRV from RRI of one minute.

The brain wave feature amount estimation unit 23 estimates θ waves of the subject using a linear regression model in which HR and RRV calculated by the heart rate feature amount calculation unit 22 are used as explanatory variables and the power of θ waves of brain waves of the subject is used as an explained variable. Therefore, in the system for calculating the amount of retained physical activity 100a of the present embodiment, it is possible to obtain the information of θ waves of the subject even if the brain waves of the subject are not actually measured. The brain wave feature amount estimation unit 23 can estimate the brain waves of the subject using various machine learning methods without being limited to the method described above.

In the same manner as in the first embodiment described above, the physical activity consumption amount calculation unit 13 calculates the consumption amount of physical activity of the subject from the power of θ waves estimated by the brain wave feature amount estimation unit 23. When a subject exercises, it is detected by an acceleration sensor or the like. From the maximum acceleration, the cumulative value of acceleration, or the like, the physical activity consumption amount calculation unit 13 can estimate the exercise load of the subject. The physical activity consumption amount calculation unit 13 determines in which of a stopped state, a walking state, and a high-load exercise state the subject is. The physical activity consumption amount calculation unit 13 calculates the degree of fatigue (consumption amount of physical activity) of the subject from the cumulative time of these states. The retained physical activity amount calculation unit 16 calculates the amount of retained physical activity of the subject by subtracting the consumption amount of physical activity calculated by the physical activity consumption amount calculation unit 13 from the reference amount of physical activity.

Figure 12:
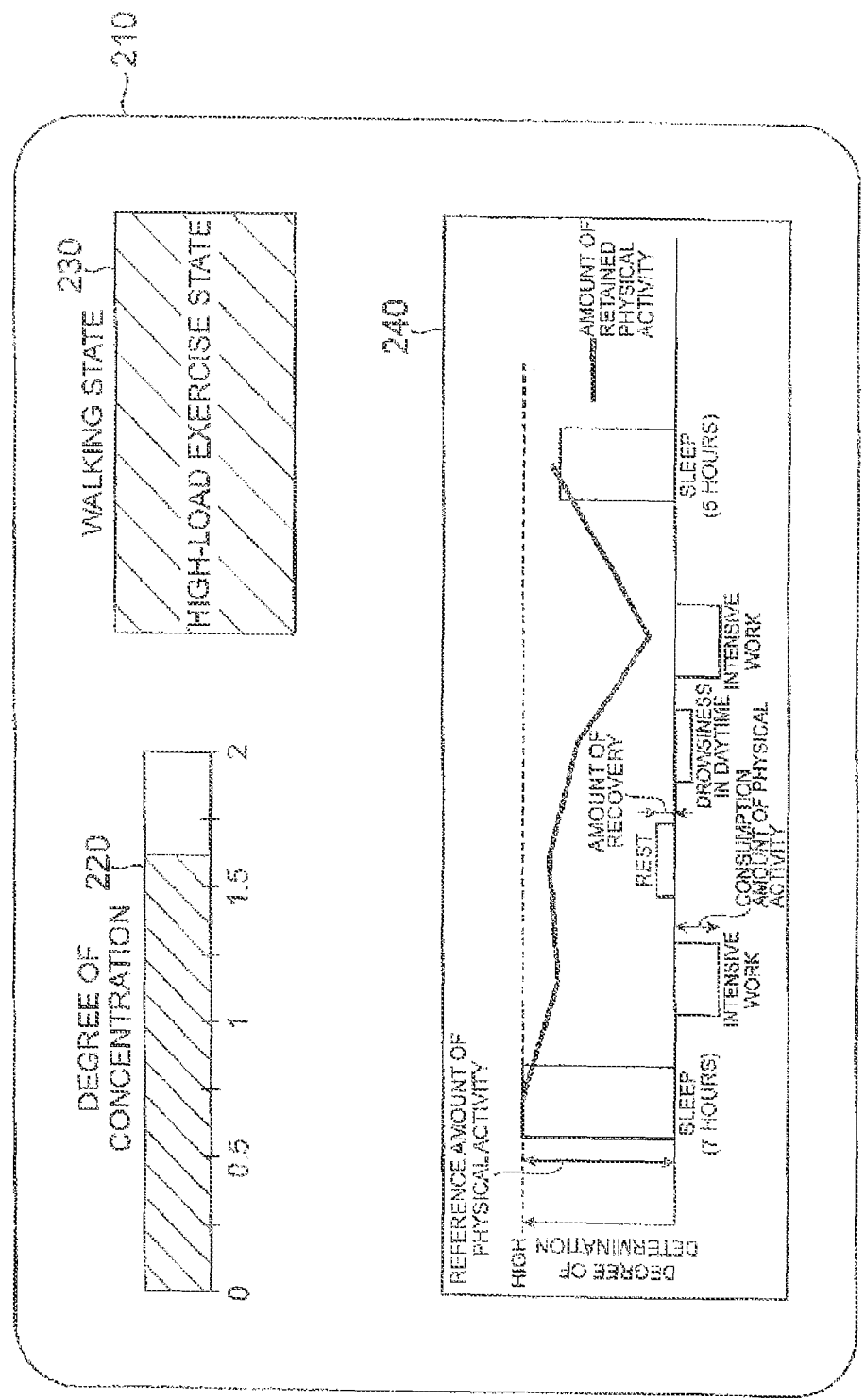
FIG. 12 is a diagram showing a display screen displayed on a display device of the second embodiment.

Specifically, the information display unit 19 is a liquid crystal display of a mobile terminal or a wrist watch. For example, a display screen 210 shown in FIG. 12 is displayed on the information display unit 19. The display screen 210 includes a degree-of-concentration display frame 220, a walking state display frame 230, and a retained physical activity amount display frame 240. The degree-of-concentration display frame 220 shows the degree of concentration of the subject. The walking state display frame 230 displays in which of a stopped state, a walking state, and a high-load exercise state the subject is. The retained physical activity amount display frame 240 displays a change in the degree of concentration or the amount of retained physical activity of the subject as a graph.

Specifically, the stimulus presentation unit 18 is a sound speaker or a vibrator, and presents a stimulus to maintain or improve the concentration of the subject when the amount of retained physical activity calculated by the retained physical activity amount calculation unit 16 becomes equal to or less than a predetermined threshold value, or when the amount of change in the amount of retained physical activity calculated by the retained physical activity amount calculation unit 16 becomes equal to or greater than a predetermined threshold value, or when the degree of concentration or the consumption amount of physical activity of the subject calculated by the physical activity consumption amount calculation unit 13 becomes equal to or less than a predetermined threshold value, or when the amount of change in the degree of concentration or the consumption amount of physical activity of the subject calculated by the physical activity consumption amount calculation unit 13 becomes equal to or greater than a predetermined threshold value.

In the present embodiment, for example, when a subject wakes up in the morning, it is possible to check the amount of retained physical activity of the subject since the amount of retained physical activity is displayed on the dial of the wrist watch. In addition, it is possible to check and look back on the degree of self-recovery or the quality of sleep from the content of sleep of the previous day. The subject can obtain the history of the amount of retained physical activity or advice on exercise or rest from the information display unit 19. In the present embodiment, if time permits, the subject plays a simple game displayed on the information display unit 19. The retained physical activity amount calculation unit 16 corrects the current amount of retained physical activity from the reaction time of the subject during the game.

In the present embodiment, when the amount of retained physical activity calculated by the retained physical activity amount calculation unit 16 becomes equal to or less than a predetermined value, the stimulus presentation unit 18 notifies that the amount of retained physical activity has become equal to or less than the predetermined value. Therefore, the subject or a person associated with the subject, such as a relative of the subject, can immediately see that the amount of physical activity retained by the subject has been reduced.

In the system of the present embodiment, respective components of the system do not necessarily need to be one device, and may be separately present. Therefore, convenience is improved.

Hereinafter, a third embodiment of the present invention will be described. In the present embodiment, data regarding the amount of physical activity of the subject from the past is stored in a server connected to a network, and the amount of retained physical activity of the subject is estimated from the data. Therefore, in the present embodiment, t, a possibility that a notification can be sent before the subject reaches an activity limit is increased.

As shown in FIG. 13, a system for calculating the amount of retained physical activity 100b of the present embodiment includes a wireless electrocardiogram sensor 21, a mobile terminal 60, a network 170, and a server 180. In addition, the system for calculating the amount of retained physical activity 100b of the present embodiment selectively includes a wireless brain wave measuring device 110, a wireless calorie calculation device 130, a wireless pupil observation device 140, and the like. The wireless brain wave measuring device 110, the wireless calorie calculation device 130, the wireless pupil observation device 140, and the like can be devices installed in vehicles, accommodations, medical institutions, ordinary homes, and the like, and can also be devices built into the mobile terminal 60.

The wireless brain wave measuring device 110 includes a brain wave sensor 112 and a brain wave feature amount calculation unit 114. The brain wave sensor 112 and the brain wave feature amount calculation unit 114 calculate the feature amount of the brain waves of the subject in the same manner as the feature amount calculation unit 12 described in the first embodiment.

The wireless calorie calculation device 130 includes a camera input unit 132 and a calorie calculation unit 134. The camera input unit 132 captures an image of a food that the subject eats. The calorie calculation unit 134 calculates the amount of calories that the subject has taken in from the image of the food captured by the camera input unit 132.

The wireless pupil observation device 140 includes a pupil sensor 142 and a pupil feature amount calculation unit 144. The pupil sensor 142 detects the movement of the pupil of the subject. The pupil feature amount calculation unit 144 calculates the feature amount of the movement of the pupil detected by the pupil sensor 142.

When the wireless brain wave measuring device 110, the wireless calorie calculation device 130, the wireless pupil observation device 140, and the like are devices provided in vehicles, accommodations, medical institutions, ordinary homes, and the like, the wireless brain wave measuring device 110, the wireless calorie calculation device 130, the wireless pupil observation device 140, and the like perform measurement when a subject carrying the mobile terminal 60 drops in at a place where these devices are installed, and transmit the measurement result to the mobile terminal 60 by short-distance wireless communication, such as Bluetooth (registered trademark).

The mobile terminal 60 is a mobile phone, a wrist watch, a mobile personal computer, or the like that a subject or a person associated with the subject, such as a relative of the subject, carries. The mobile terminal 60 includes a parameter identification unit 24 in addition to the heart rate feature amount calculation unit 22 and the like of the second embodiment described above. The parameter identification unit 24 corrects parameters, such as correction coefficients $a_1$ to $a_3$, of the state equation for calculating the amount of retained physical activity (amount of retained physical activity=$a_1$×reference amount of physical activity−$a_2$×consumption amount of physical activity+$a_3$×amount of recovery), for example.

The physical activity amount prediction calculation unit 17 transmits data of the schedule of the subject, the consumption amount of physical activity, the amount of recovery, the amount of retained physical activity, and the like to the server 180 through the network 170 as learning data. The learning data, such as the schedule of the subject, the consumption amount of physical activity, the amount of recovery, and the amount of retained physical activity, is stored in the server 180. When a certain amount of learning data is stored, the server 180 transmits the correction values of parameters, such as the correction coefficients $a_1$ to $a_3$, based on the learning data to the physical activity amount prediction calculation unit 17. The parameter identification unit 24 corrects parameters, such as the correction coefficients $a_1$ to $a_3$, of the state equation for calculating the amount of retained physical activity based on the correction values received through the physical activity amount prediction calculation unit 17.

On the information display unit 19, it is possible to write the daily schedule of the subject with a key panel or the like. The mobile terminal 60 is connected to a personal computer, which is connected to the network 170, by short-distance wireless communication, such as Bluetooth (registered trademark). When the subject starts measurement using the wireless electrocardiogram sensor 21 or the like, the consumption amount of physical activity of the subject is calculated from the heart rate feature amount of the subject at that time. Data of the action in the schedule of the subject, the consumption amount of physical activity, the amount of recovery, the amount of retained physical activity, and the like is stored in the server 180, as learning data, through the network 170. When a certain amount of learning data is stored, the parameter identification unit 24 performs parameter identification of the state equation for calculating the amount of retained physical activity based on the data. The retained physical activity amount calculation unit 16 calculates the amount of retained physical activity of the subject based on the identified parameters.

According to the present embodiment, the parameter identification unit 24 corrects parameters for calculating the amount of retained physical activity based on the history of the consumption amount of physical activity and the amount of recovery of the subject from the past. Therefore, it is possible to calculate the amount of physical activity that closely reflects the circumstances of the subject.

According to the present embodiment, since the system for calculating the amount of retained physical activity 100b can acquire the biological information of the subject from various devices, the accuracy of the calculation of the amount of physical activity of the subject is improved.

In addition, it is needless to say that the present invention is not limited to the above-described embodiments and various changes can be made without departing from the spirit or scope of the present invention.

INDUSTRIAL APPLICABILITY

According to the device for calculating the amount of retained physical activity, the method for calculating the amount of retained physical activity, and the system for calculating the amount of retained physical activity of the embodiments of the present invention described above, it is possible to calculate the amount of physical activity retained by the subject instantaneously.

REFERENCE SIGNS LIST

10: biological activity amount management device
11: biological information acquisition unit
12: feature amount calculation unit
13: physical activity consumption amount calculation unit
14: recovery amount calculation unit
15: reference physical activity amount setting unit
16: retained physical activity amount calculation unit
17: physical activity amount prediction calculation unit
18: stimulus presentation unit
19: information display unit
21: wireless electrocardiogram sensor
22: heart rate feature amount calculation unit
23: brain wave feature amount estimation unit
24: parameter identification unit
50, 60: mobile terminal
100a, 100b: system for calculating amount of retained physical activity
110: wireless brain wave measuring device
112: brain wave sensor
114: brain wave feature amount calculation unit
130: wireless calorie calculation device
132: camera input unit
134: calorie calculation unit
140: wireless pupil observation device
142: pupil sensor
144: pupil feature amount calculation unit
170: network
180: server
210: display screen
220: degree-of-concentration display frame
230: walking state display frame
240: retained physical activity amount display frame

The invention claimed is:

1. An activity tracker comprising:
at least one biological information sensor including at least one of: an electrocardiogram sensor, a brain wave sensor and a pupil sensor;
at least one of a sound speaker or a vibrator; and
one or more processors programmed to:
perform a real time, continuous biological information collection and state estimation process that includes multiple instances of both: (i) acquiring biological information of the subject from any of the at least one biological information sensor, and (ii) estimating, based on the acquired biological information, a state of the subject from among a plurality of predefined states, the acquired biological information including one or more physiological indicators required to estimate the state of the subject from the plurality of predefined states, the one or more physiological indicators including one or more of: heart rate information, heartbeat pulse wave information, breathing information, and brain wave information, the plurality of predefined states of the subject including at least one sleep state and at least one awakened state, wherein the performing of the repetitive biological information collection and state estimation process comprises, at multiple time intervals:
determining whether the estimated state of the subject is any of the at least one awakened state;

based on determining that the estimated state of the subject is any of the at least one awakened state after a predetermined amount of time that the estimated state of the subject has remained in any of the at least one sleep state, set an initial reference remaining amount of retained physical activity of a subject based on a previously-stored value, an average value over several normal days, or a database of demographic information about subjects that includes ages and genders of subjects;

determining whether at least one of two conditions is satisfied, the two conditions being: (i) the subject has remained in one of the at least one awakened state for at least two consecutive time intervals, or (ii) a time that the last at least one awakened state occurred is not longer ago than the predetermined amount of time;

based on determining that at least one of the two conditions is satisfied and the estimated state of the subject is any of the at least one awakened state, calculating and storing, in an area for consecutive values in a memory, a current consumption amount of physical activity consumed by the subject at that time, based on the acquired biological information;

based on determining that the estimated state of the subject is not any of the at least one awakened state: calculating and storing, in the area for the consecutive values, an amount of recovery, which is an amount of physical activity recovered by the subject at that time, based on the acquired biological information;

determining whether the consecutive values are more than a predetermined number; and based on determining that the consecutive values are more than the predetermined number:

determining and storing a current remaining amount of retained physical activity retained by the subject, by subtracting the total consumption amount of physical activity in the consecutive values as modified by a first correction coefficient from either the initial reference remaining amount of physical activity or the most recent previously-stored amount of retained physical activity as modified by a second correction coefficient, while adding the total amount of recovery in the consecutive values as modified by a third correction coefficient;

determining whether the current remaining amount of retained physical activity becomes equal to or less than a predetermined activity limit threshold; and based on determining that the current remaining amount of retained physical activity becomes equal to or less than the predetermined activity limit threshold, controlling the at least one of the sound speaker or the vibrator to present a physical stimulus to the subject in response to the current remaining amount of physical activity retained by the subject becoming than or equal to the predetermined activity limit threshold, thereby notifying the subject that the amount of physical activity retained by the subject has been reduced while maintaining or improving the concentration of the subject, the presentation of the physical stimulus including at least one of: a physical sound stimulus output by the sound speaker, or a physical vibration stimulus output by the vibrator, wherein the one or more processors are further programmed to:

cause a light stimulus to be output;

estimate a current reaction speed-based degree of concentration of the subject based on a reaction speed, which is obtained by a reaction speed of the subject with respect to the light stimulus; and correct the correction coefficients for calculating the current remaining amount of retained physical activity based on the estimated reaction speed-based current degree of concentration of the subject, which corresponds to an estimated remaining amount of retained physical activity.

2. The activity tracker according to claim 1, wherein the estimation of the current reaction speed-based degree of concentration of the subject is based on a correlation between a subjective degree of concentration of the subject and estimated brain waves that are estimated based on the obtained reaction speed.

3. The activity tracker according to claim 1, wherein the current amount of recovery is calculated based on either sleep spindles or θ waves of brain waves of the biological information acquired in the sleep state.

4. The activity tracker according to claim 1, wherein the current amount of recovery is calculated based on a depth of sleep of the subject estimated from the biological information acquired in the sleep state.

5. The activity tracker according to claim 1, wherein the one or more processors are further programmed to:

set the most recent previously-stored remaining amount of retained physical activity as the initial reference remaining amount of physical activity; and periodically reset the initial reference remaining amount of physical activity.

6. The activity tracker according to claim 1, wherein the one or more processors are further programmed to: calculate the correction coefficients based on a past history of the consecutive values of consumption amounts of physical activity and amounts of recovery of the subject.

7. The activity tracker according to claim 1, wherein the computing device is further configured to instantaneously display the current remaining amount of retained physical activity for the subject on a display.

8. The activity tracker according to claim 1, wherein the one or more processors are further programmed to: calculate the current remaining amount of retained physical activity of the subject according to the following equation: the current remaining amount of retained physical activity=$a_1$×the initial reference remaining amount of physical activity or the most recent previously-stored remaining amount of retained physical activity−$a_2$×the total consumption amount of physical activity+$a_3$×the total amount of recovery in the consecutive values, and wherein $a_1$ is the first correction coefficient, $a_2$ is the second correction coefficient, and $a_3$ is the third correction coefficient.

9. The activity tracker according to claim 7, wherein the activity tracker is a mobile personal device, and comprises the display.

10. The activity tracker according to claim 1, wherein the one or more processors are further configured to: estimate θ waves of the subject using a linear regression model in which heart rate is used as an explanatory variable and a power of θ waves of brain waves of the subject is used as an explained variable, thereby obtaining information of θ waves of the subject even if the brain waves of the subject are not actually measured.

11. A method of tracking activity, the method comprising:
performing, by one or more processors, a real time, continuous biological information collection and state estimation process that includes multiple instances of both: (i) acquiring biological information of the subject from any of the at least one biological information sensor, and (ii) estimating, based on the acquired biological information, a state of the subject from among a plurality of predefined states, the acquired biological information including one or more physiological indicators required to estimate the state of the subject from the plurality of predefined states, the one or more physiological indicators including one or more of: heart rate information, heartbeat pulse wave information, breathing information, and brain wave information, the plurality of predefined states of the subject including at least one sleep state and at least one awakened state, wherein the performing of the repetitive biological information collection and state estimation process comprises, at multiple time intervals:
  determining, by the one or more processors, whether the estimated state of the subject is any of the at least one awakened state;
  based on determining that the estimated state of the subject is any of the at least one awakened state after a predetermined amount of time that the estimated state of the subject has remained in any of the at least one sleep state, setting, by the one or more processors, an initial reference remaining amount of retained physical activity of a subject based on a previously-stored value, an average value over several normal days, or a database of demographic information about subjects that includes ages and genders of subjects;
  determining, by the one or more processors, whether at least one of two conditions is satisfied, the two conditions being: (i) the subject has remained in one of the at least one awakened state for at least two consecutive time intervals, or (ii) a time that the last at least one awakened state occurred is no longer ago than the predetermined amount of time;
  based on determining that at least one of the two conditions is satisfied and the estimated state of the subject is any of the at least one awakened state, calculating and storing, by the one or more processors in an area for consecutive values in a memory, a current consumption amount of physical activity consumed by the subject at that time, based on the acquired biological information;
  based on determining that the estimated state of the subject is not any of the at least one awakened state: calculating and storing, by the one or more processors in the area for the consecutive values, an amount of recovery, which is an amount of physical activity recovered by the subject at that time, based on the acquired biological information;
  determining, by the one or more processors, whether the consecutive values are more than a predetermined number; and
  based on determining that the consecutive values are more than the predetermined number:
    determining and storing, by the one or more processors, a current remaining amount of retained physical activity retained by the subject, by subtracting the total consumption amount of physical activity in the consecutive values as modified by a first correction coefficient from either the initial reference remaining amount of physical activity or the most recent previously-stored amount of retained physical activity as modified by a second correction coefficient, while adding the total amount of recovery in the consecutive values as modified by a third correction coefficient;
    determining, by the one or more processors, whether the current remaining amount of retained physical activity becomes equal to or less than a predetermined activity limit threshold; and
    based on determining that the current remaining amount of retained physical activity becomes equal to or less than the predetermined activity limit threshold, controlling, by the one or more processors, the at least one of the sound speaker or the vibrator to present a physical stimulus to the subject in response to the current remaining amount of retained physical activity becoming less than or equal to the predetermined activity limit threshold, thereby notifying the subject that the amount of physical activity retained by the subject has been reduced while maintaining or improving the concentration of the subject, the presentation of the physical stimulus including at least one of: a physical sound stimulus output by the sound speaker, or a physical vibration stimulus output by the vibrator, wherein the method further comprises:
      causing, by the one or more processors, a light stimulus to be output;
      estimating, by the one or more processors, a current reaction speed-based degree of concentration of the subject based on a reaction speed, which is obtained by at least one of: a reaction speed of the subject with respect to the light stimulus; and
      correcting, by the one or more processors, based on the estimated reaction speed-based current degree of concentration of the subject, which corresponds to an estimated remaining amount of retained physical activity, the correction coefficients for calculating the current remaining amount of retained physical activity.

12. The method of tracking activity according to claim 11, further comprising:
  determining, by the one or more processors, a past history of the subject based on previously stored amounts of physical activity consumption and recovery; and
  calculating, by the one or more processors, the correction coefficients based on the past history of the subject, wherein the current remaining amount of retained physical activity is determined based, at least in part, on the correction coefficients.

13. The method of tracking activity according to claim 11, wherein the current remaining amount of retained physical activity is calculated by:
  multiplying, by the one or more processors, the initial reference remaining amount of physical activity or the most recent previously-stored remaining amount of retained physical activity by the first correction coefficient to obtain a predictive reference amount;
  multiplying, by the one or more processors, the total consumption amount of physical activity in the consecutive values by the second correction coefficient to obtain a predictive consumption amount;

multiplying, by the one or more processors, the total amount of recovery in the consecutive values by the third correction coefficient to obtain a predictive amount of recovery;

subtracting, by the one or more processors, the predictive consumption amount from the predictive reference amount to obtain a predictive physical activity result; and adding, by the one or more processors, the predictive amount of recovery to the predictive physical activity result.

14. An activity tracking system comprising:

a vibrator;

a calorie calculation device that includes a camera configured to capture an image of food that a subject eats;

an electrocardiogram sensor;

a brain wave sensor;

a pupil sensor that detects movement of a pupil of the subject, wherein each of the electrocardiogram sensor, the brain wave sensor, and the pupil sensor are configured to measure biological information of a subject, and the calorie calculation device is configured to calculate an amount of calories that the subject has taken in from the image of the food captured by the camera; and one or more processors programmed to:

perform a real time, continuous biological information collection and state estimation process that includes multiple instances of both: (i) acquiring biological information of the subject from at least one of the calorie calculation device, the electrocardiogram sensor, the brain wave sensor or the pupil sensor, and (ii) estimating, based on the acquired biological information, a state of the subject from among a plurality of predefined states, the acquired biological information including one or more physiological indicators required to estimate the state of the subject from the plurality of predefined states, the one or more physiological indicators including one or more of: heart rate information, heartbeat pulse wave information, breathing information, and brain wave information, the plurality of predefined states of the subject including at least one sleep state and at least one awakened state, wherein the performing of the repetitive biological information collection and state estimation process comprises, at multiple time intervals:

determining whether the estimated state of the subject is any of the at least one awakened state, based on determining that the estimated state of the subject is any of the at least one awakened state after a predetermined amount of time that the estimated state of the subject has remained in any of the at least one sleep state, setting an initial reference remaining amount of retained physical activity of a subject based on a previously-stored value, an average value over several normal days, or a database of demographic information about subjects that includes ages and genders of subjects;

determining whether at least one of two conditions is satisfied, the two conditions being: (i) the subject has remained in one of the at least one awakened state for at least two consecutive time intervals, or (ii) a time that the last at least one awakened state occurred is no longer ago than the predetermined amount of time;

based on determining that at least one of the two conditions is satisfied and the estimated state of the subject is any of the at least one awakened state, calculating and storing, in an area for consecutive values in a memory, a current consumption amount of physical activity consumed by the subject at that time, based on the acquired biological information;

based on determining that the estimated state of the subject is not any of the at least one awakened state: calculating and storing, in the area for the consecutive values, an amount of recovery, which is an amount of physical activity recovered by the subject at that time, based on the acquired biological information;

determining whether the consecutive values are more than a predetermined number; and based on determining that the consecutive values are more than the predetermined number:

determining and storing a current remaining amount of retained physical activity retained by the subject, by subtracting the total consumption amount of physical activity in the consecutive values as modified by a first correction coefficient from either the initial reference remaining amount of physical activity or the most recent previously-stored amount of retained physical activity as modified by a second correction coefficient, while adding the total amount of recovery in the consecutive values as modified by a third correction coefficient;

determining whether the current remaining amount of retained physical activity becomes equal to or less than a predetermined activity limit threshold; and based on determining that the current remaining amount of retained physical activity becomes equal to or less than the predetermined activity limit threshold, controlling the vibrator to present a physical stimulus to the subject in response to the current remaining amount of physical activity becoming less than or equal to the predetermined activity limit threshold, thereby notifying the subject that the amount of physical activity retained by the subject has been reduced while maintaining or improving the concentration of the subject, the presentation of the physical stimulus including a physical vibration stimulus output by the vibrator, wherein the one or more processors are further programmed to: correct the correction coefficients for calculating the current remaining amount of retained physical activity based on the history of consumption amounts of physical activity and amounts of recovery of the subject from the past.

15. The activity tracking system according to claim 14, wherein the initial reference remaining amount of physical activity is based, at least in part, on previously acquired biological information associated with past physical activity of the subject.

16. The activity tracking system according to claim 14, wherein the one or more processors are further programmed to: calculate the current remaining amount of retained physical activity of the subject according to the following equation: the current remaining amount of retained physical activity=$a_1$×the initial reference remaining amount of physical activity or the most recent previously-stored remaining amount of retained physical activity−$a_2$×the total consumption amount of physical activity+$a_3$×the total amount of recovery in the consecutive values, and wherein $a_1$ is the first correction coefficient, $a_2$ is the second correction coefficient, and $a_3$ is the third correction coefficient.

17. The activity tracking system according to claim 14, wherein the one or more processors are programmed to: estimate θ waves of the subject using a linear regression model in which heart rate is used as an explanatory variable and a power of θ waves of brain waves of the subject is used as an explained variable, thereby obtaining information of θ waves of the subject even if the brain waves of the subject are not actually measured.

\* \* \* \* \*